US00PP23575P2

(12) United States Plant Patent
Stemkens

(10) Patent No.: US PP23,575 P2
(45) Date of Patent: Apr. 30, 2013

(54) ***VERBENA* PLANT NAMED 'VEAZ0009'**

(50) Latin Name: *Verbena×hybrida*
Varietal Denomination: VEAZ0009

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 7 days.

(21) Appl. No.: 13/373,721

(22) Filed: Nov. 28, 2011

(51) Int. Cl.
*A01H 5/00* (2006.01)

(52) U.S. Cl. ..... Plt./308

(58) Field of Classification Search ..... Plt./308
See application file for complete search history.

*Primary Examiner* — Kent L Bell

(74) *Attorney, Agent, or Firm* — Joshua L. Price

(57) ABSTRACT

A new *Verbena* plant named 'VEAZ0009' particularly distinguished by the tri-colored flowers that are white, red and red-purple, medium green foliage, medium sized creeping and trailing plant habit with moderate branching.

1 Drawing Sheet

Latin name of the genus and species of the plant claimed: *Verbena×hybrida.*

Varietal denomination: 'VEAZ0009'.

BACKGROUND OF THE NEW PLANT

The present invention comprises a new *Verbena*, botanically known as *Verbena×hybrida*, and hereinafter referred to by the variety name 'VEAZ0009'.

'VEAZ0009' is a product of a planned breeding program. The new cultivar has tri-colored flowers that are white, red and red-purple, medium green foliage, medium sized creeping and trailing plant habit with moderate branching.

'VEAZ0009' originated from an open pollinated hybridization made in August 2007 in a controlled breeding environment in Enkhuizen, Netherlands. The female parent was the unpatented, proprietary plant designated 'K0400-5' having uniform purple colored flowers with an eye in the center and a less vigorous growth habit.

The male parent of 'VEAZ0009' is unknown.

The resultant seed was sown in February 2008. 'VEAZ0009' was selected as one flowering plant within the progeny of the stated open pollination in August 2008 in a controlled environment in Enkhuizen, Netherlands.

The first act of asexual reproduction of 'VEAZ0009' was accomplished when vegetative cuttings were propagated from the initial selection in August 2008 in a controlled environment in Enkhuizen, Netherlands.

BRIEF SUMMARY OF INVENTION

Horticultural examination of plants grown from cuttings of the plant initiated in the August 2008, and continuing thereafter, has demonstrated that the combination of characteristics as herein disclosed for 'VEAZ0009' are firmly fixed and are retained through successive generations of asexual reproduction.

'VEAZ0009' has not been observed under all possible environmental conditions. The phenotype may vary significantly with variations in environment such as temperature, light intensity, and day length.

A Plant Breeder's Right for this cultivar was applied for in Canada on Jun. 23, 2011, #11-7316. 'VEAZ0009' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0009' with colors being as true as possible with an illustration of this type.

Figure 1:
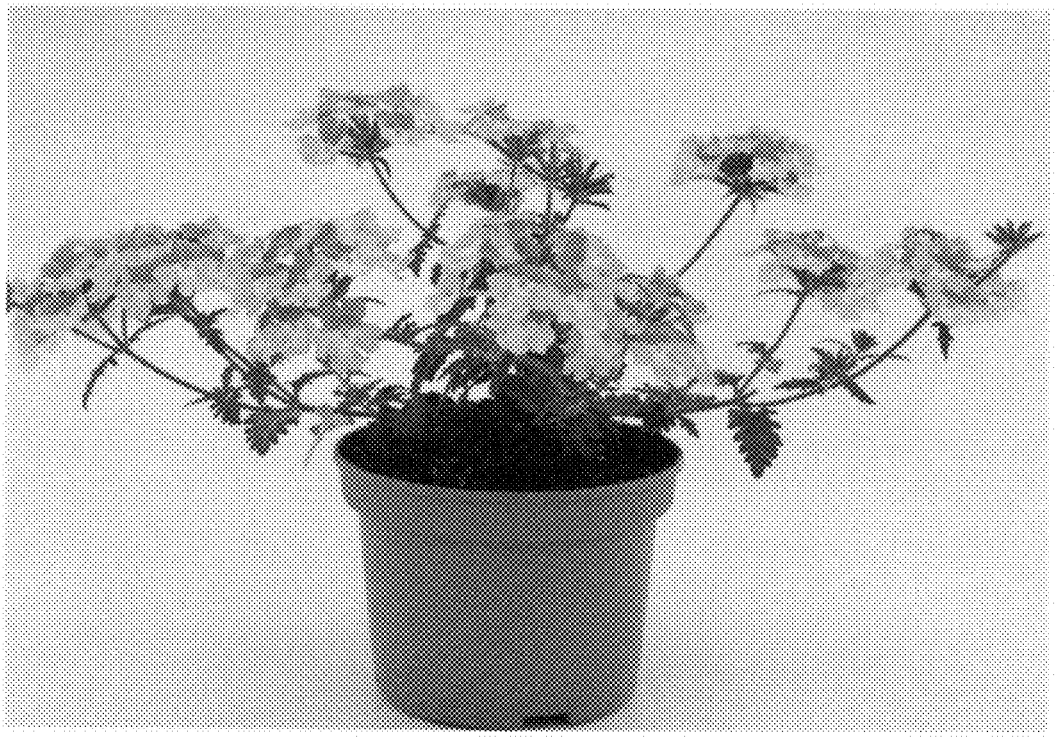
Figure 2:
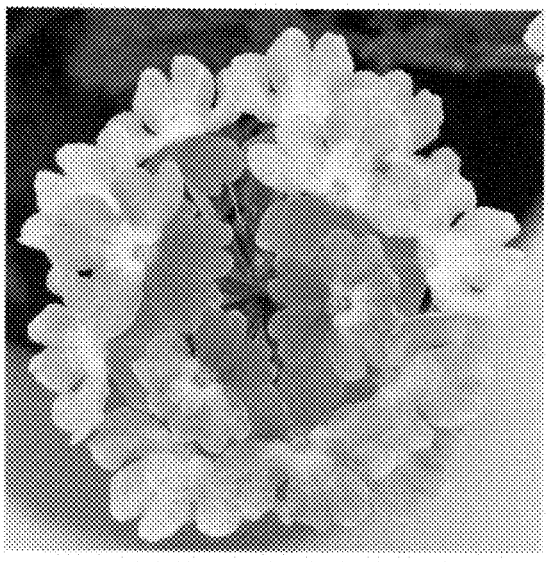

The photographic drawing shows in FIG. 1. A flowering plant of the new variety and in FIG. 2. A close-up of the flowers.

DETAILED BOTANICAL DESCRIPTION

The aforementioned photographs were taken May 2011 from plants growing in a greenhouse trial in Andijk, Netherlands. The plants were growing in 12 cm pots and were approximately 13 weeks of age.

The plant descriptions and measurements were taken in May 2011 in Andijk, Netherlands on about 10-11 week old plants that had been planted into 12 cm pots and grown on benches in a greenhouse at a minimum temperature of about 12° C. From April on, a minimum night temperature of 8° C. was held, while day temperatures were higher, depending on the outdoor temperature.

Color references are made to The Royal Horticultural Society Colour Chart (R.H.S.) 2001.

TABLE 1

DIFFERENCES BETWEEN THE NEW VARIETY 'VEAZ0009' AND A SIMILAR VARIETY

| | 'VEAZ0009' | 'FLAGDENA' (U.S. (Plant Pat. No. 22,438) |
|---|---|---|
| Floret size | Smaller | Larger |
| Floret color | Upper two petals RHS 45B, lower three petals | Upper two petals RHS 57A, lower three petals |

TABLE 1-continued

| DIFFERENCES BETWEEN THE NEW VARIETY 'VEAZ0009' AND A SIMILAR VARIETY | |
|---|---|
| 'VEAZ0009' | 'FLAGDENA' (U.S. (Plant Pat. No. 22,438) |
| RHS N155D but whiter with large margins of RHS N57C | mostly white with small margins of RHS 65A |

Plant:
- *Form, growth and habit*.—Herbaceous, mainly creeping or ascending, later trailing.
- *Plant height*.—About 4.0-8.0 cm.
- *Plant height* (*inflorescence included*).—About 6.0-10.0 cm.
- *Plant width*.—About 60.0-65.0 cm.

Roots:
- *Number of days to initiate and produce roots*.—About 10-14 days at about 22 degrees C.
- *Type*.—Fine, fibrous, free branching.
- *Color*.—RHS N155B.

Foliage:
- *Arrangement*.—Opposite, decussate.
- *Immature, leaf color, upper surface*.—RHS 137C.
- *Lower surface*.—RHS 138A.
- *Mature, leaf color, upper surface*.—RHS 137A.
- *Lower surface*.—RHS 137C.
- *Length*.—3.3-4.3 cm.
- *Width*.—2.3-3.1 cm.
- *Shape*.—Ovate to deltoid.
- *Base shape*.—Nearly truncate.
- *Apex shape*.—Obtuse to rounded.
- *Margin*.—Slightly pinnatifid and irregularly incised.
- *Texture, upper surface*.—Short hair.
- *Lower surface*.—Short, stiff hair mainly along the veins; some glandular hairs.
- *Color of veins, upper surface*.—About RHS 137D becoming indistinct.
- *Color of veins, lower surface*.—RHS 138B.
- *Petiole color*.—RHS 138B.
- *Petiole length*.—0.2-0.4 cm.
- *Diameter*.—0.2 cm.
- *Texture*.—Hirtellous.

Stem:
- *Characteristics*.—Side branches develop potentially at every node.
- *Number of main stems*.—10-15.
- *Color of stem*.—RHS 143C.
- *Length of stem*.—Approximately 30.0-35.0 cm.
- *Diameter*.—0.25-0.30 cm.
- *Length of internodes*.—3.0-4.0 cm.
- *Texture*.—Densely covered with hair; hirsute.
- *Color of peduncle*.—RHS 138A.
- *Length of peduncle*.—4.0-7.0 cm.
- *Peduncle diameter*.—0.2 cm.
- *Texture*.—Densely covered with short, glandular hair; hirtellous.

Inflorescence:
- *Type*.—Umbel-like, but actually a spike, umbrella-shaped to roughly semi-spherical.
- *Blooming habit*.—Continuously through the summer months.
- *Lastingness of individual blooms on the plant*.—About 4 days in the greenhouse.
- *Fragrance*.—Very light.
- *Quantity of inflorescences per plant*.—About 35.
- *Quantity of flowers and buds per inflorescence*.—About 25-30.
- *Inflorescence horizontal diameter*.—6.5 cm.
- *Inflorescence depth* (*height*).—3.0 cm.

Bud (just when starting to show color):
- *Color*.—RHS 52C to RHS 52D.
- *Length*.—1.3-1.5 cm.
- *Width*.—0.2-0.3 cm at flower end.
- *Shape*.—Mainly tube-shaped with a bulbous end.

Floret:
- *Form and type*.—Sessile; salverform, composed of 5 partly fused petals with a base of a narrow tube.
- *Immature floret, color upper surface*.—Upper two petals RHS 45B, lower three petals RHS N155B but whiter with large margin of RHS N57C.
- *Immature floret, color lower surface*.—Upper two petals RHS 46B, and lower three petals RHS56C with RHS 55B margins.

Mature floret:
- *Floret diameter*.—1.7-2.0 cm.
- *Floret depth*.—1.4-1.8 cm.
- *Floret, color upper surface*.—Upper two petals RHS 45B, lower three petals RHS N155D but whiter with large margins of RHS N57C.
- *Floret, lower surface*.—Upper two petals RHS 65A and partly RHS 46B at margins, lower three petals RHS 65D.
- *Length of petals*.—0.9-1.0 cm.
- *Width of petals*.—0.9 cm.
- *Petal shape*.—Obcordate.
- *Apex shape*.—Emarginate.
- *Margin*.—Entire.
- *Petal texture, upper surface*.—Smooth and glabrous.
- *Texture, lower surface*.—Smooth and glabrous.
- *Corolla tube length*.—1.8 cm.
- *Corolla tube, color inside*.—RHS 150D.
- *Tube, color outside*.—RHS N155B.
- *Corolla tube, texture inside*.—Glabrous.
- *Texture outside*.—Glabrous basally; glandular hairs at the throat opening.

Calyx:
- *Type*.—Five sepals whose margins are fused to each other along their length, with a transparent membrane of less than 0.1 cm in width and with one smaller sepal attached to the base of the calyx.
- *Color of sepals*.—RHS 138A.
- *Length of sepals*.—1.2 cm.
- *Width of sepals*.—0.2-0.3 cm.
- *Sepal shape*.—Linear, fused.
- *Apex shape*.—Acute.
- *Margins*.—Entire.
- *Texture, inner surface*.—Glabrous.
- *Texture, outer surface*.—Densely covered with short hair.

Reproductive organs:
- *Pistil*.—1.
- *Length*.—1.7 cm.
- *Style color*.—RHS 144D.
- *Style length*.—1.3-1.5 cm.
- *Stigma color*.—RHS 144A.
- *Stamens*.—Anthers and filaments fused to upper half of corolla tube; four anthers with two pollen sacs per anther.
- *Color of filaments*.—RHS 150D to RHD 155B.

*Length filaments.*—0.1 cm.
*Anther color.*—RHS 144D.
*Length of anthers.*—0.1-0.15 cm.
*Color of pollen.*—RHS 1A.
*Pollen amount.*—Moderate.
*Fertility/seed set.*—Some seed set has been observed.
*Disease/pest resistance.*—Has not been observed on this hybrid.

What is claimed is:

1. A new and distinct variety of *Verbena* plant named 'VEAZ0009' substantially as illustrated and described herein.

* * * * *